(12) United States Patent
Seto et al.

(10) Patent No.: US 7,306,947 B2
(45) Date of Patent: Dec. 11, 2007

(54) AUTOMATIC ANALYSIS APPARATUS

(75) Inventors: Yoshihiro Seto, Minamiashigara (JP); Tomoyuki Takiue, Minamiashigara (JP); Tsutomu Tanaka, Minamiashigara (JP); Katsumi Suzuki, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 871 days.

(21) Appl. No.: 10/755,679

(22) Filed: Jan. 13, 2004

(65) Prior Publication Data

US 2004/0191925 A1    Sep. 30, 2004

(30) Foreign Application Priority Data

Jan. 14, 2003    (JP)    ............................. 2003-006008
Jan. 6, 2004    (JP)    ............................. 2004-001244

(51) Int. Cl.
    *G01N 35/02*    (2006.01)
(52) U.S. Cl. ............................ 436/48; 422/67; 422/64; 436/43; 436/514; 436/169

(58) Field of Classification Search ................ 436/68.1
    See application file for complete search history.

(56) References Cited

U.S. PATENT DOCUMENTS

2002/0031844 A1    3/2002    Komatsu et al.
2002/0098116 A1    7/2002    Sugaya et al.

*Primary Examiner*—Walter D. Griffin
*Assistant Examiner*—Bobby Ramdhanie
(74) *Attorney, Agent, or Firm*—Sughrue Mion Pllc.

(57) ABSTRACT

When a dry analysis element contained in an element cartridge to be loaded in a sample tray of an automatic analysis apparatus projects from a take out port, the element is returned to its proper position, thereby preventing conveyance failure and information readout failure, with the result that higher operation reliability is ensured. An element mounting portion is equipped with a correcting means, such as a restricting projection. The correcting means contacts and pushes a dry analysis element which projects from an element cartridge back to its predetermined position therein, in association with a loading operation of the element cartridge.

18 Claims, 10 Drawing Sheets

AUTOMATIC ANALYSIS APPARATUS

BACKGROUND OF THE INVENTION

1. Field of the Invention

The present invention relates to an automatic analysis apparatus like a biochemical analysis apparatus in which a sample such as blood or urine is spotted onto a calorimetric dry analysis element or an electrolytic dry analysis element, and the concentration, ion activity and the like of a specific biochemical component contained in the sample are determined. The present invention particularly relates to a mechanism for correcting the position of a dry analysis element contained in an element cartridge.

2. Description of the Related Art

Traditionally, there have been developed and practically implemented colorimetric dry analysis elements with which the content of a specific biochemical component or specific solid component contained in a sample can be quantitatively analyzed by merely spotting a droplet of the sample, and electrolytic dry analysis elements with which the activity of a specific ion contained in a sample can be determined by merely spotting a droplet of the sample. The biochemical analysis apparatuses using such dry analysis elements are preferably used in medical institutions, laboratories and the like owing to their capability of analyzing samples easily and quickly.

The colorimetry method using calorimetric dry analysis elements is as follows: a droplet of a sample is spotted on a dry analysis element; the analysis element is held at a constant temperature for a predetermined time in an incubator so that a coloring reaction (pigment forming reaction) occurs; the optical density of the color formed by the coloring reaction is optically measured by exposing the analysis element to measuring light, containing a wavelength which is pre-selected according to the combination of the component to be analyzed and the reagent contained in the analysis element; and the concentration of the component to be analyzed is determined on the basis of the optical density according to a calibration curve representing the relationship between the concentration of the specific biochemical component and the optical density.

On the other hand, in the potentiometry method using an electrolytic dry analysis element, the activity of a specific ion contained in a sample spotted on an ion selective electrode pair of a dry analysis element is potentiometrically measured instead of measuring the optical density.

In either of colorimetry or potentiometry, the sample is contained in a sample container (e.g., a blood-collecting tube) and set in the analysis apparatus, while an analysis element required for the measurement is loaded in the apparatus. The dry analysis element is carried from the loaded position to a spotting position while the sample is delivered by a spotting nozzle from the set position to the spotting position for spotting on the dry analysis element.

In the biochemical analysis apparatus, a plurality of dry analysis elements as mentioned above for measuring the same or different items are contained in a stacked form in element cartridges, and such element cartridges are set in a sample tray. Then, a cartridge containing therein desired dry analysis elements is moved to a predetermined element-takeout position by the linear and rotational movement of the sample tray. F Thereby the desired dry analysis elements are removed out of this element cartridge and conveyed to a spotting station. Examples of such known element cartridges include those provided for horizontally moving the lowermost dry analysis element, for example, by a transfer bar, and taking the element out of a take-out port provided in the lower portion of the sidewall, in order to make the takeout position constant (see U.S. Patent Laid-Open Nos. 20020031844 and 20020098116.)

For the element cartridge holding therein dry analysis elements as mentioned above, a problem may arise in association with the fact that the lowermost dry analysis element is movable to project outward from the element take-out port.

More specifically, when handling the element cartridge for the purpose of loading the dry analysis elements into the element cartridge, setting the element cartridge holding therein the dry analysis elements in the sample tray or the like, are loaded in the element cartridge, the lowermost dry analysis element within the cartridge may unintentionally penetrate into the element take-out port or protrude outward therefrom. Consequently, such displacement of the dry analysis element could cause conveyance failure and/or information readout failure. For example, some dry analysis elements carry on their bottom surfaces analysis information including the measuring items and the like, and such analysis information is read out before removing the dry analysis element to be used for measurement control. In the case that the dry analysis element is displaced as mentioned above, the analysis information recorded on the bottom surface thereof cannot be read properly, and may also cause trouble in the conveyance of the element.

SUMMARY OF THE INVENTION

In view of the foregoing, an object of the present invention is to provide an automatic analysis apparatus wherein a dry analysis element contained in an element cartridge is returned to its proper position when the dry analysis element becomes displaced and misaligned with respect to the proper position, thereby preventing conveyance failure and information readout failure.

The present invention provides a first automatic analysis apparatus for: mounting an element cartridge holding dry analysis elements required for measurement of a sample onto an element mounting portion, the element cartridge being equipped with an element take-out port which allows a single dry analysis element to pass through; removing one or more of the dry analysis elements from the element mounting portion; and conveying the one or more removed dry analysis elements to a following process; wherein the element mounting portion has a correcting means for returning a protruding dry analysis element to a predetermined position within the element cartridge, in association with the loading operation of the element cartridge when the element cartridge is mounted on the element mounting portion.

A construction may be adopted wherein:

the element cartridge is further equipped with a penetration path extending to the element take-out port in the cartridge loading direction; and the element mounting portion is equipped with a correcting means for entering the penetration path, abutting a dry analysis element which protrudes into the element take out port, and pushing the dry analysis element to the predetermined position within the element cartridge, in association with the loading operation of the element cartridge when the element cartridge is mounted on the element mounting portion.

The correcting means may comprise a restricting projection that tapers to project further outward as it extends. Alternatively, the correcting means may comprise a spring member for pressing and urging an element cartridge. Meanwhile, it is preferable that the penetration path for element cartridges comprises a slit groove.

It is preferable that the element mounting portion is equipped with an element outlet for a dry analysis element, which has been removed from an element cartridge mounted thereon, to pass through; and the correcting means is provided above the element outlet of the element mounting portion so as to extend vertically.

It is further preferable that the penetration path includes inclined guide surfaces at the lower part thereof which extend to the element take-out port so as to diverge from one another.

The present invention provides a second automatic analysis apparatus for: mounting an element cartridge holding dry analysis elements required for measurement of a sample onto an element mounting portion; removing one or more of the dry analysis elements from the element mounting portion; and conveying the one or more removed dry analysis elements to a following process; wherein:

the element mounting portion is equipped with a pusher for pushing and returning a dry analysis element that protrudes from the element cartridge to a predetermined position within the element cartridge, in association with the loading operation of the element cartridge when the element cartridge is mounted on the element mounting portion.

It is preferable that the pusher operates after detecting mounting of the element cartridge on the element mounting portion.

In accordance with the invention as described above, the element mounting portion has the correcting means for returning a protruding dry analysis element to a predetermined position within the element cartridge, in association with the loading operation of the element cartridge when the element cartridge is mounted on the element mounting portion. There are cases in which the dry analysis elements protrude from the element cartridge while loading them into the element cartridge or during mounting of the element cartridge onto the element mounting portion. Even in these cases, the correcting means of the element mounting portion penetrates into the penetration path of the element cartridge, contacts the dry analysis element protruding into or from the element take-out port, and acts to push back the dry analysis element, in association with the loading operation of the element cartridge onto the element mounting portion. When the loading of the element cartridge is completed, the dry analysis element is positioned at its proper position, such that the conveyance failure and information readout failure which could be caused by displacement are prevented. Therefore, the information carried on the dry analysis element within the element cartridge can be properly read, and the dry analysis element can be properly removed and conveyed from the element cartridge, which ensures higher operation reliability.

A construction may be adopted wherein:

the element cartridge is further equipped with a penetration path extending to the element take-out port in the cartridge loading direction; and the element mounting portion is equipped with a correcting means for entering the penetration path, abutting a dry analysis element which protrudes into the element take out port, and pushing the dry analysis element to the predetermined position within the element cartridge, in association with the loading operation of the element cartridge when the element cartridge is mounted on the element mounting portion. In this case, the dry analysis element can be pushed back to the interior of the element cartridge.

DESCRIPTION OF THE PREFERRED EMBODIMENTS

Figure 1:
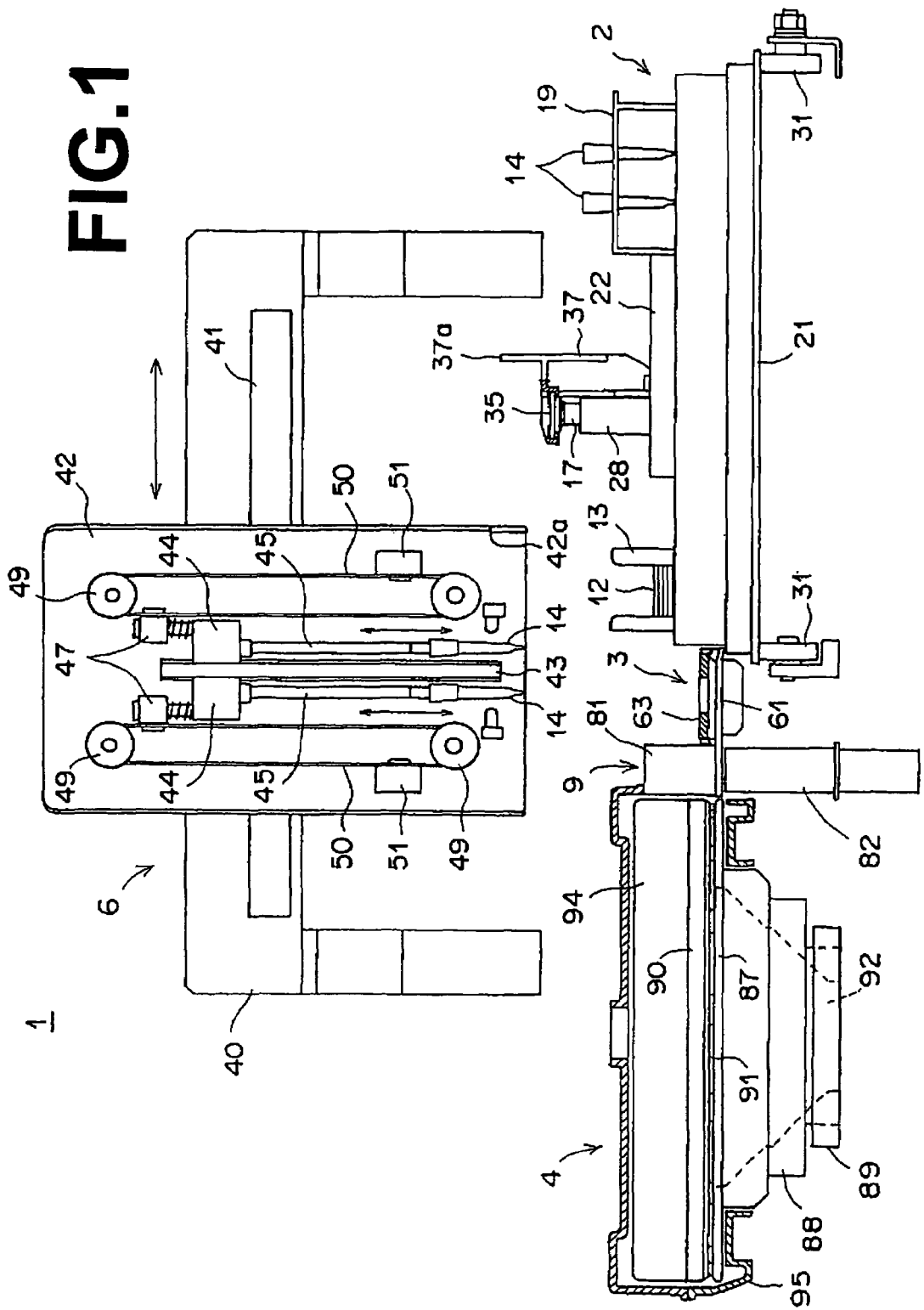
FIG. 1 is a front view, partially in cross section, showing a schematic construction of a biochemical analysis apparatus according to a first embodiment of the present invention.
Figure 2:
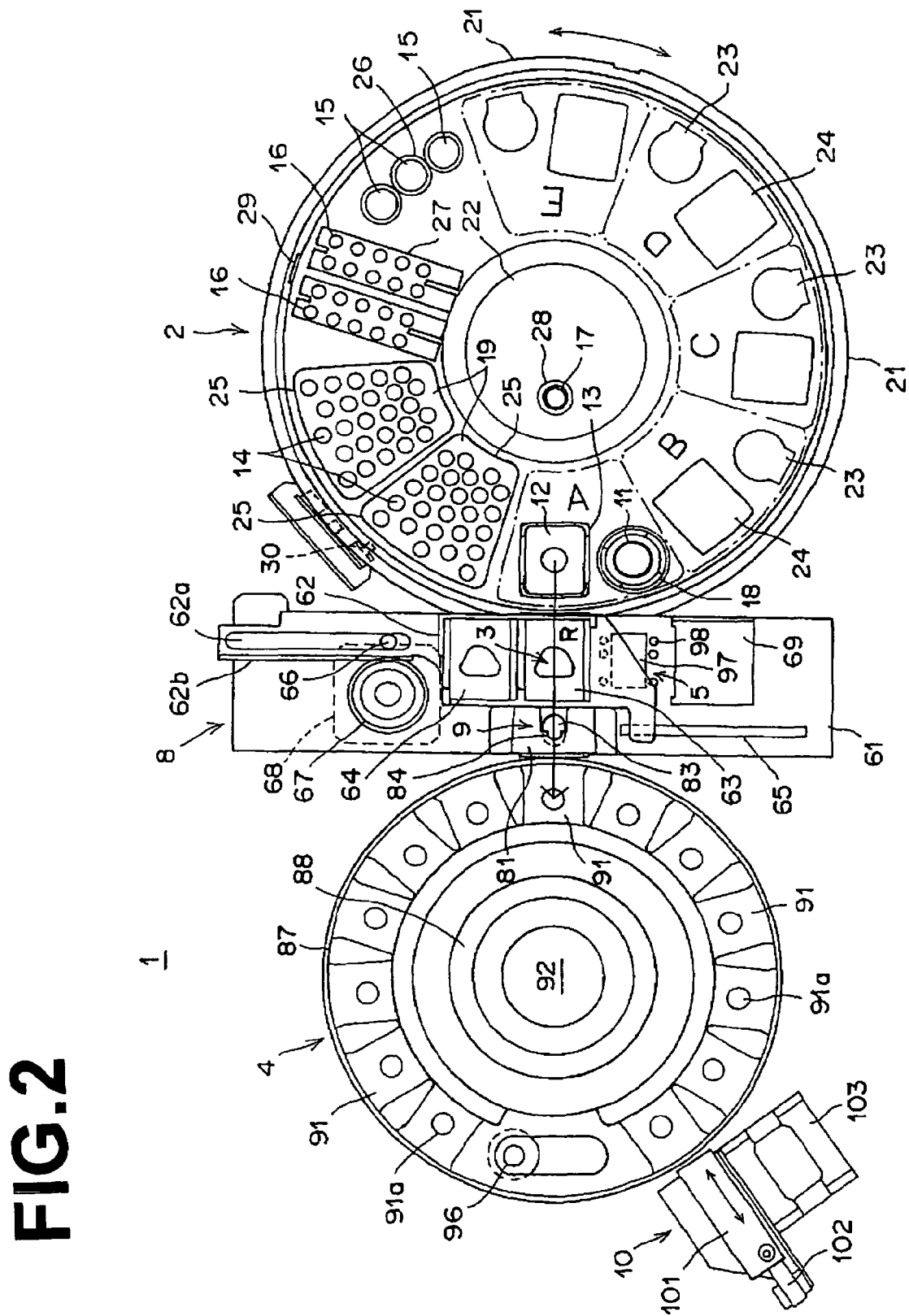
FIG. 2 is a plan view showing the mechanism of an essential part of the analysis apparatus of FIG. 1.
Figure 3:
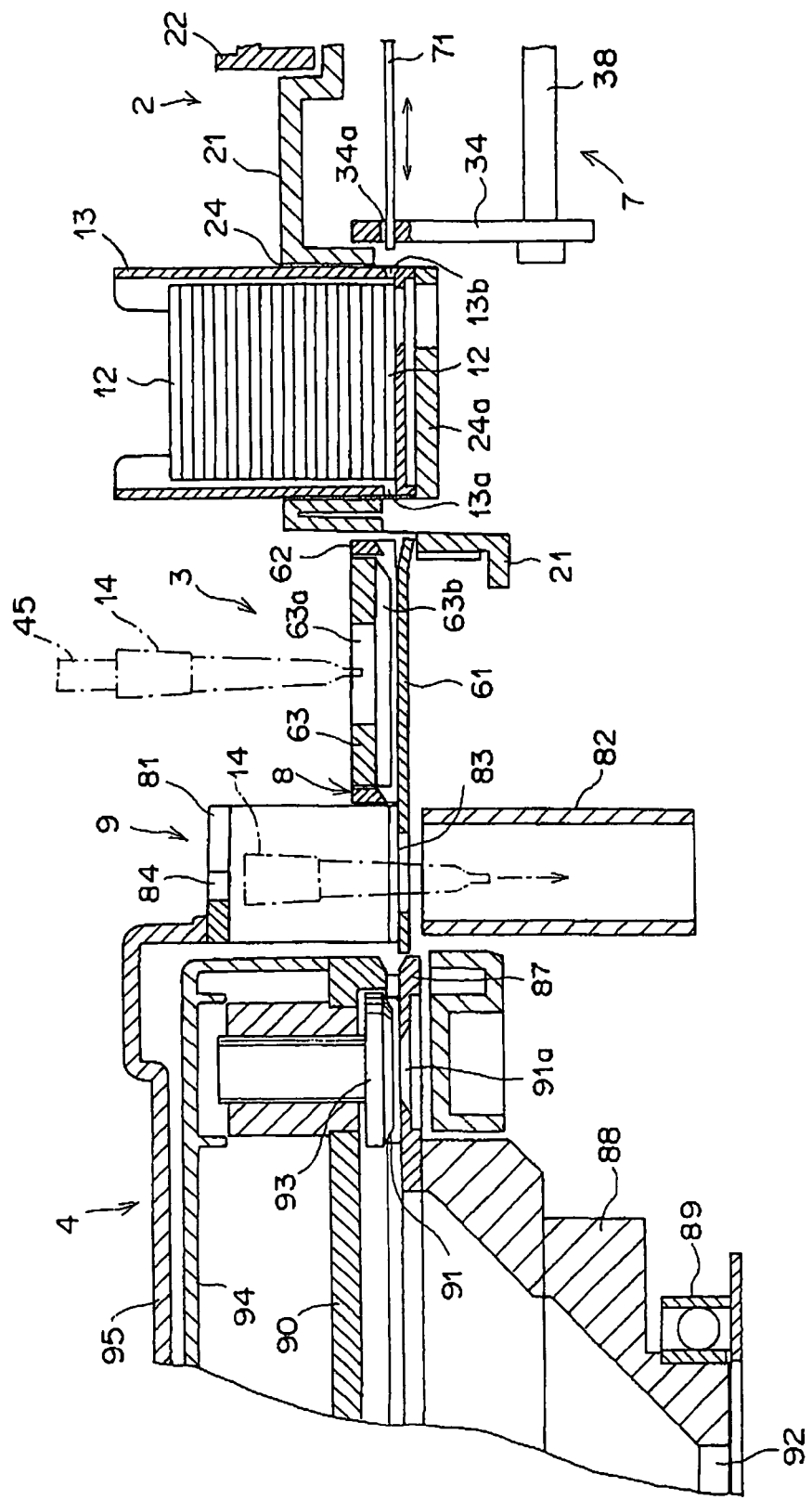
FIG. 3 is a cross-sectional front view showing a transfer path for dry analysis elements of the biochemical analysis apparatus of FIG. 1.
Figure 4:
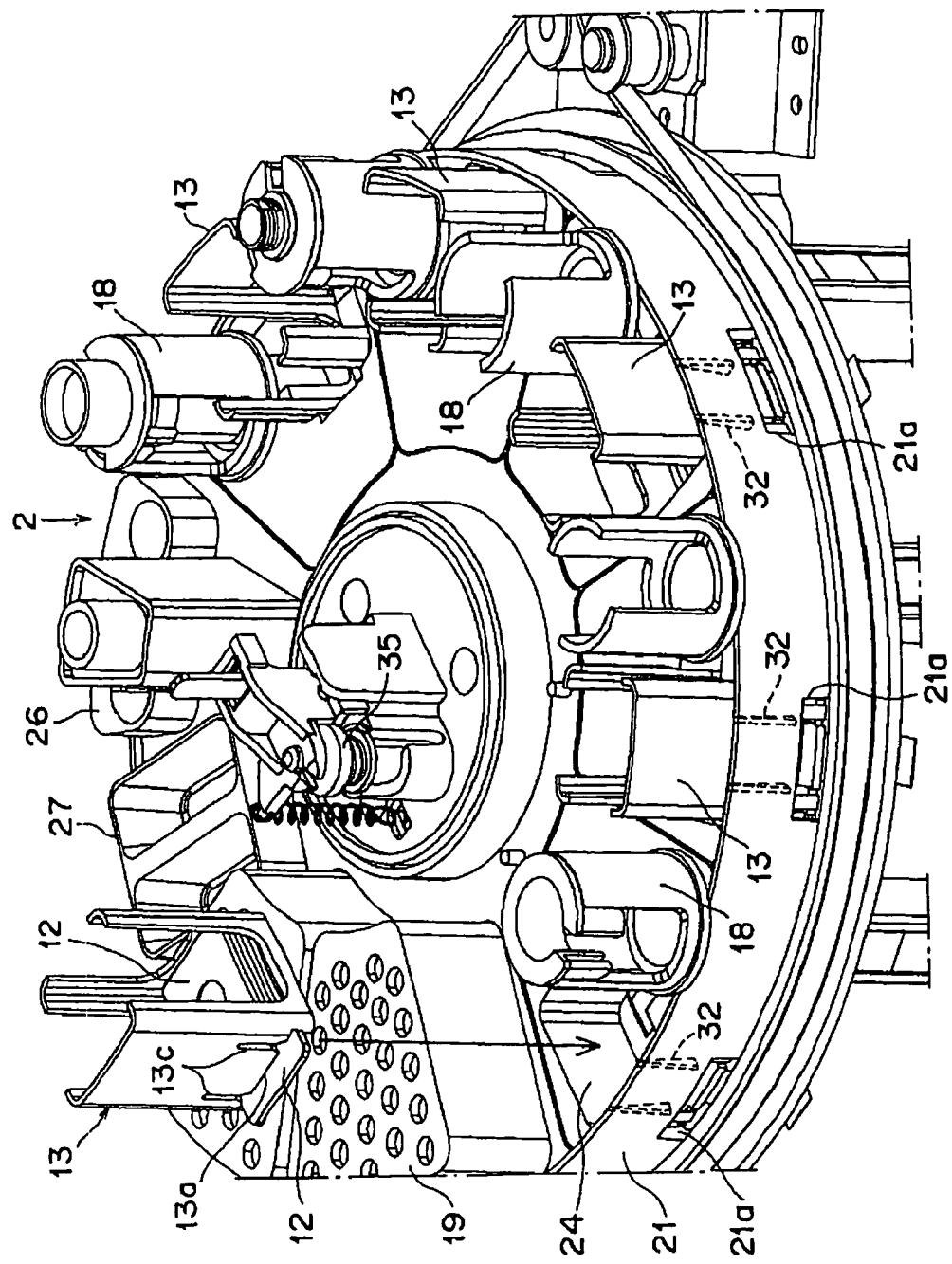
FIG. 4 is a perspective view of an essential part of a sample tray when an element cartridge is being loaded thereon.
Figure 5:
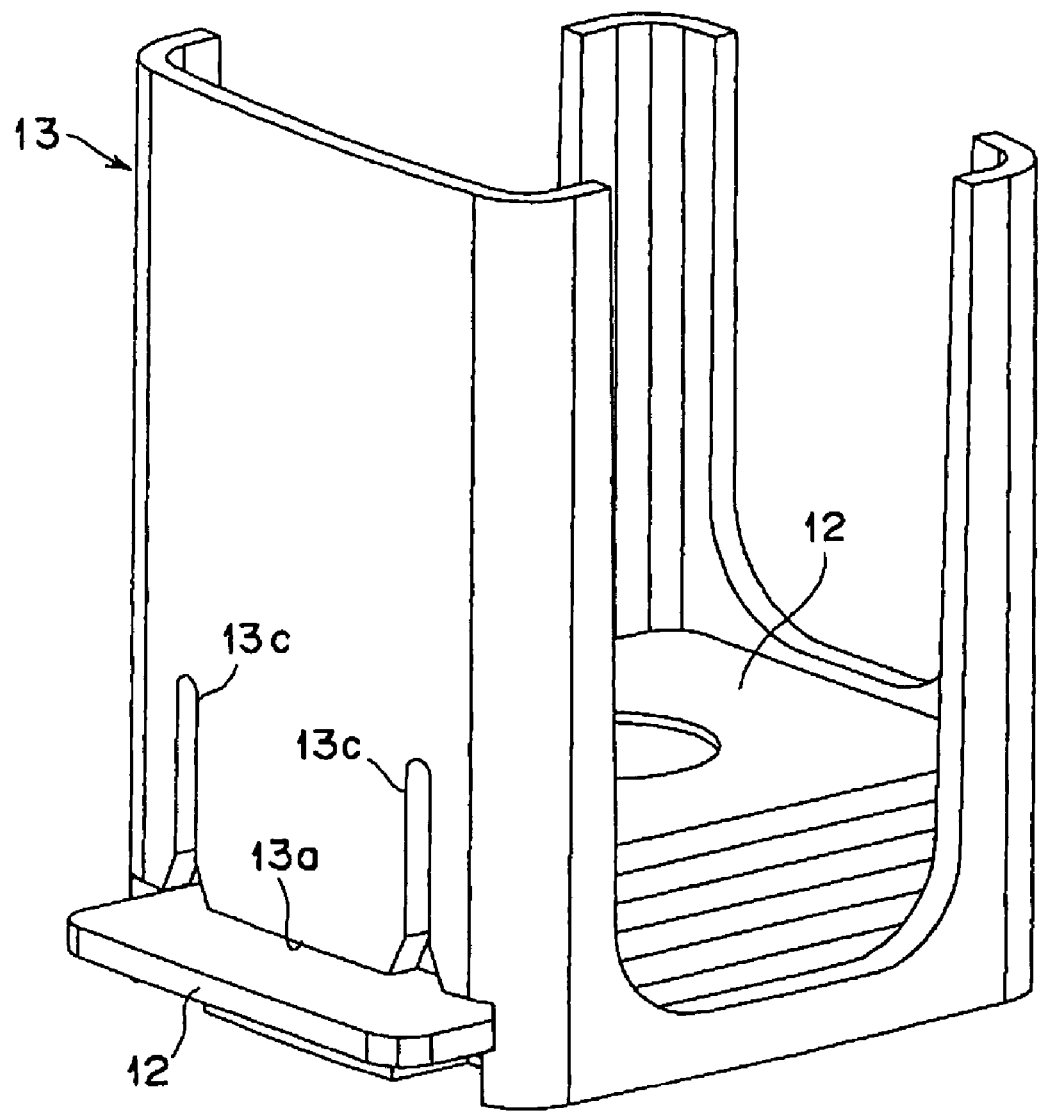
FIG. 5 is a perspective view showing the element cartridge when a dry analysis element projects therefrom.
Figure 6A:
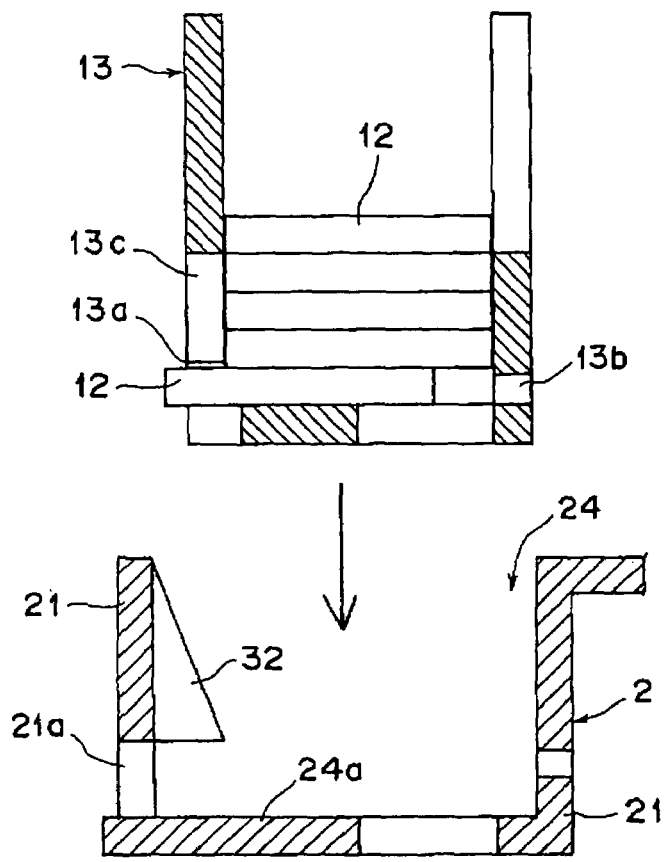
FIGS. 6A and 6B are schematic views showing the correcting operation with respect to the dry analysis element associated with the element cartridge loading operation.
Figure 6B:
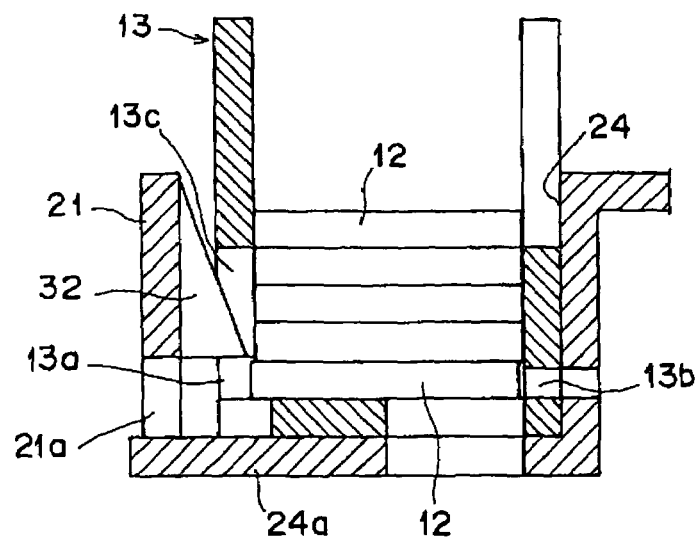

Preferred embodiments of the present invention will be described below with reference to the drawings. As an illustrative automatic analysis apparatus according to this embodiment, a biochemical analysis apparatus will be described hereinafter with reference to the accompanying drawings. FIG. 1 is a front view, partially in cross section, showing a schematic construction of a biochemical analysis apparatus according to the first embodiment of the present invention, FIG. 2 is a plan view showing an essential mechanism of the biochemical analysis apparatus, FIG. 3 is a cross-sectional front view showing a transfer path for dry analysis elements of the biochemical analysis apparatus, FIG. 4 is a perspective view of an essential part of a sample tray when an element cartridge is being loaded thereon, FIG. 5 is a perspective view showing the element cartridge when a dry analysis element projects therefrom; and FIGS. 6A and 6B are schematic views showing an alignment action with respect to the dry analysis element associated with the element cartridge loading process.

First, a description of a general configuration of a biochemical analysis apparatus 1 will be given in connection with FIGS. 1 to 3. This biochemical analysis apparatus 1 comprises a sample tray 2, a spotting station 3, a first incubator 4, a second incubator 5, a spotting unit 6, an element conveyance mechanism 7, a transfer mechanism 8, a tip disposal area 9, an element discarding mechanism 10, etc.

The sample tray 2 is circular in shape, and provided with a sample container 11 holding therein a sample, an element cartridge 13 holding therein unused dry analysis elements 12 (e.g., colorimetric dry analysis elements and electrolytic dry analysis elements), and consumables (e.g., nozzle tips 14, dilution containers 15, mixing cups 16, and reference solution containers 17). The sample container 11 is set in the sample tray via a sample adaptor 18, and a number of nozzle tips 14 are also set in the sample tray in a state in which the nozzle tips are held in a tip rack 19.

The spotting station 3 where a sample such as plasma, whole blood, serum, urine or the like is spotted on the dry analysis element 12 is disposed on an extended line from the centerline of the sample tray 2. At the spotting station 3, in the case of a calorimetric dry analysis element 12, a sample is spotted thereon by the spotting unit 6 and in the case of an electrolytic dry analysis element 12, a sample and reference solution are spotted thereon by the spotting unit 6. The tip disposal area 9 into which the nozzle tips 14 are discarded is disposed following and adjacent to the spotting station 3.

The first incubator 4 is circular in shape and disposed on the aforementioned extended line on a side of the tip disposal area 9 opposite the sample tray 2. The first incubator 4 holds therein a calorimetric dry analysis element 12, wherein the analysis element is kept at a constant temperature (incubated) for a predetermined time and subjected to a calorimetric measurement. The second incubator 5 (see FIG. 2) is disposed adjacent to the side of the spotting station 3, and holds therein an electrolytic dry analysis element 12, wherein the analysis element is incubated for a predetermined time and subjected to the potential difference measurement (potentiometry).

Although no details are illustrated, the element transfer mechanism 7 (see FIG. 3) has an element transfer member 71 (transfer bar) positioned within the sample tray 2. The element transfer member 71 serves to remove a dry analysis element 12 out of the element cartridge 13 of the sample tray 2 and to feed the dry analysis element to the spotting station 3 and in turn to the first incubator 4 along a linear element conveyance path R (see FIG. 2) which extends between the center of the sample tray 2 and the center of the first incubator 4 through the spotting station 3 and the tip disposal area 9. The element transfer member 71 is slidably supported by a guide rod 38 and reciprocally moved by a driving mechanism (not shown). One end of the element transfer member 71 is slidingly engaged in a guide hole 34a of a vertical plate 34.

The transfer mechanism 8, which also serves as the spotting station 3, is provided for transferring an electrolytic dry analysis element 12 from the spotting station 3 to the second incubator 5 in the direction perpendicular to the element transfer path R The spotting unit 6 is provided at the upper part of the analysis apparatus and includes a spotting nozzle 45 adapted to move vertically. The spotting nozzle 45 is also capable of traveling along the same straight line as the aforementioned element transfer path R, and performs spotting of the sample and reference solution on the analysis element, diluting the sample with the diluent, and mixing the diluted sample. The spotting nozzle 45 has a nozzle tip 14 fitted onto the tip end thereof, for suctioning and discharging the reference solution and the like with respect to the inside of the nozzle tip 14. The spotting nozzle 45 is provided with syringe means not shown which suctions and discharges such reference solution and the like. The used nozzle tip 14 is removed and dropped for disposal at the tip disposal area 9.

The first incubator 4 is provided with the element discarding mechanism 10 (see FIG. 2) which pushes the calorimetric dry analysis element 12 after measurement toward the central portion of the first incubator 4 and drops the element for disposal. This element may be discarded by the aforementioned element transfer mechanism 7. Meanwhile, the electrolytic dry analysis element 12 after being subjected to the measurement in the second incubator 5 is moved and discarded into a discarding hole 69 by the transfer mechanism 8.

A blood-filtering unit (not shown) for separating blood plasma from blood is provided beside the sample tray 2.

In the following, the construction of each section of the system will be specifically described. The sample tray 2 comprises a rotary disk 21 which is rotated in opposite directions, and a disk-shaped non-rotatable part 22 disposed at the center part thereof.

As shown in FIG. 2, the rotary disk 21 includes: five sample mounting sections 23 (A-E) for holding via the sample adapter 18 a sample container 11 (e.g., blood-collecting tube) containing therein a sample; five element mounting sections 24, which are respectively positioned adjacent the sample mounting sections, for holding the element cartridge 13 that accommodates in a stacked form unused dry analysis elements 12 usually including various types as required corresponding to a measuring item of each sample measurement; two tip mounting sections 25 for holding the tip rack 19 that includes nozzle tip holding holes for respectively receiving a number of nozzle tips 14; three diluent mounting section 26 for holding the diluent container 15 containing therein a diluent, a cup mounting section 27 for holding a mixing cup 16 (a molded product provided with a plurality of cup-like recesses) used for mixing therein the diluent and sample. These sections are arranged along an arc.

Each element mounting section 24 of the rotary disk 21 comprises an element outlet 21a (see FIG. 4) formed in the peripheral wall in front of the element take-out port 13a (see FIG. 4) of the element cartridge 13; and a rib-shaped restricting member 32 (to be described in detail later), for contacting a dry analysis element 12 which projects from the element cartridge 13 and returning it to the interior of the element cartridge 13, formed above the element outlet 21a within the element mounting section 24.

The non-rotatable part 22 includes a reference mounting section 28 of hollow-cylindrical shape for holding therein the reference solution container 17 containing the reference solution. The reference mounting section 28 is located on the line extended from the element transfer path R within the range of the movement of the spotting nozzle 45 and provided with an anti-evaporation cap 35 (see FIG. 1) for opening and closing the opening of the reference solution container 17.

The anti-evaporation cap 35 is held and urged in the closing direction by a support member 37 and the lower end of the support member 37 is pivotally supported by the non-rotatable part 22. An upper end engagement portion 37a of the support member 37 can be brought into contact with a bottom end corner 42a of a movable frame 42 of the spotting unit 6. The movable frame 42 approaches the support member for suctioning the reference solution such that the support member 37 is allowed to pivot towards its opening direction. Accordingly, the anti-evaporation cap 35 opens the reference solution container 17 and the spotting nozzle 45 is allowed to suction the reference solution. In other states, the anti-evaporation cap 35 closes the opening of the reference solution container 17 to prevent evaporation of the reference solution, which inhibits degradation of the measurement accuracy due to the change in concentration of the reference solution.

The rotary disk 21 is supported at its perimeter by a support roller 31 and rotatably held at the central portion thereof by a supporting shaft (not shown). A timing belt is wound around the outer circumference of the rotary disk 21 and rotates the rotary disk 21 in opposite directions with the aid of a driving motor. The non-rotatable part 22 is non-rotatably mounted to the supporting shaft mentioned above.

The aforementioned element cartridge 13 is, as shown in FIG. 5, shaped in a rectangular chamber with an open top. A plurality of unused dry analysis elements 12, which are usually arranged in a form stacked in a mixed state, are inserted in the cartridge 13 through the open top. The element take-out port 13a and a penetration path 13c (detailed later) which extends vertically from the element take-out port 13a are provided at a front lower end part of the element holding chamber 21.

When the element cartridge 13 is mounted to the element mounting section 24, the lower end of the cartridge is held on a bottom wall 24a of the element mounting section 24, and the lower most dry analysis element 12 is positioned at the same level as that of the element transfer surface of the element transfer member 71. The front wall of the element cartridge has at the lower most part the element take-out port 13a which allows only a single analysis element to pass therethrough, while the rear wall thereof has an opening 13b through which the element transfer member 71 can penetrate. In the bottom wall, a window is formed such that a lot number etc. represented by bar cords, dots or the like provided on the bottom surface of the dry analysis element 12 can be read from below.

On the other hand, the sample adapter 18 is formed in a tubular shape, and the sample container 11 is inserted therein from above. The sample adapter 18 has an identification portion (not shown). Information such as a type (process information) of the sample, a type (size) of the sample container 11 and the like are set; the identification of the sample is read at the start of the measurement by an identification sensor 30 (see FIG. 2), which is disposed on the outer circumference of the sample tray 2, in order to determine whether the sample is diluted, whether the blood plasma is filtered or the like; the liquid level variations associated with the size of the sample container 17 is calculated; and control depending thereon is performed.

The spotting station 3 and the transfer mechanism 8 have a long supporting table 61 which extends between the sample tray 2 and the first incubator 4 in the direction perpendicular to the element transfer path R, and a sliding frame 62 is provided on the supporting table 61. A first element retainer 63 with a spotting opening 63a (see FIG. 3) and a second element retainer 64 attached to the sliding frame 62 so that they are arranged adjacent to each other and they can move as one. A recess 63b through which the dry analysis element 12 move along the element transfer path R is provided in the bottom wall of the first element retainer 63 (also the second element retainer 64) on the side facing to the supporting table 61. The sliding frame 62 is guided at one end by a guide bar 65, and comprises a pin 66 engaged in a long slit 62a disposed on the side of the other end, and a rack gear 62b with which a driving gear 67 of a driving motor 68 is engaged. The supporting table has the second incubator 5 and a discarding hole 69.

As shown in FIG. 2, when the first element retainer 64 is positioned at the spotting station 3, the colorimetric dry analysis element 12 after being subjected to spotting is pushed out and transferred to the first incubator 4 by the element transfer member 71 of the element transfer mechanism 7. On the other hand, when spotting onto the electrolytic dry analysis element 12 is performed, the sliding frame 62 is moved such that the dry analysis element 12 after spotting is slidingly moved on the supporting table 61 with the element being retained by the first element retainer 63, transferred to the second incubator 5, and subjected to the potentiometry. At this time, the second element retainer 64 is moved to the spotting station 3 (spotting position), and therefore, it is possible to spot the sample on the calorimetric dry analysis element 12 to be subsequently supplied, and to transfer the spotted element to the first incubator 4. After completion of the measurement by the second incubator 5, the sliding frame 62 is further moved such that the dry analysis element 12 after measurement is conveyed to and dropped into the discarding hole 69 for disposal.

Note that it is also possible that the second element retainer 64 is moved to the spotting station 3 when a calorimetric dry analysis element 12 and left there, and the first element retainer 63 is moved to the spotting station 3 only when the electrolytic dry analysis element is conveyed.

The spotting unit 6 (see FIG. 1) has the movable frame 42 which is supported on a horizontal guide rail 41 of a stationary frame 40 so as to be horizontally movable. Two spotting nozzles 45 are mounted on the movable frame 42 so as to be vertically movable. A vertical guide rail 43 is fixed in the center of the movable frame 42, and two nozzle-fixing blocks 44 are arranged at opposed sides of the vertical guide rail. Upper ends of the spotting nozzles are respectively fastened to the lower part of the nozzle fixing blocks 44. The nozzle-fixing block 44 has a shaft-like member which extends upward and passing through a drive transmission member 47. A compression spring interposed between the nozzle fixing block 44 and the drive transmission member 47 provides the nozzle tip 14 with an engaging force. The nozzle fixing block 44 is vertically movable together with the drive transmission member 46 as one, and when the nozzle tip 14 is fitted to the end of the spotting nozzle 45, the compression spring is compressed, which allows the drive transmission member 47 to move downward with respect to the nozzle fixing block 44. The drive transmission member 47 is fixed to the belt 50 which is tensed between the upper and lower pulleys 49, and vertically moved in association with the movement of the belt 50 driven by a motor not shown. A balance weight is mounted on the outside of the belt 50 for preventing the spotting nozzle 56 from moving downward except during driving.

The horizontal travel and independent vertical movements of the spotting nozzles 45 are controlled by the facts that the movable frame 42 is horizontally traveled by a belt driving mechanism (not shown) and the two nozzle fixing blocks 44 are vertically moved independently of one another. In this way, the two spotting nozzles 45 are allowed to horizontally travel as one and vertically move independently of one another. For example, one of the spotting nozzles 45 is for spotting the sample, and the other is for spotting the diluent or the reference solution.

The spotting nozzle 45 is formed in the shape of a rod provided with an air passage extending in the axial direction and a pipette-like nozzle tip 14 is fitted on the lower end portion thereof. The spotting nozzles 45 are connected to air tubes respectively connected to syringe pumps (not shown), and a suction force and a discharge force are selectively supplied to the spotting nozzles 45. Further, the liquid surface of the sample or the like can be detected based on variation of the suction pressure.

The tip disposal area 9 comprises an upper member 81 and a lower member 82, and is provided so as to vertically intersect with the transfer path R. A drop hole 83 having an oblong shape is provided in this tip disposal area 9 of the supporting table 61. The upper member 82 is fastened to the upper surface of the supporting table 61 and provided with an engagement cutout just above the drop hole 83. Meanwhile, the lower member 82 is provided on the lower surface of the supporting table 61 so as to surround the lower part of the drop hole 83 and serves to guide a dropping nozzle tip 14.

The spotting nozzle 45 on which the nozzle tip 14 is attached is first moved downward into the upper member 81, and then horizontally moved such that the engagement cutout 84 of the upper member 81 is engaged with the upper end of the nozzle tip 14. The spotting nozzle 45 is then moved upward, whereby the nozzle tip is removed therefrom. The removed nozzle tip 14 is dropped through the drop hole 83 for disposal.

The first incubator 4 for making a colorimetric measurement comprises a toroidal-shaped rotary member 87 at a radially outward region thereof. The rotary member 87 has an inclined rotary pipe 88 fixed on the radially inward side of the lower surface of the rotary member. The lower part of the inclined rotary cylinder 88 is rotatably supported by a bearing 89 disposed below thereof, which allows the rotary member 87 to freely rotate. An upper member 90 is provided at the upper part of the rotary member 87 so that the upper member 90 can rotate integrally with the rotary member 87. The bottom surface of the upper member 90 is flat, and the top surface of the rotary member 87 has a plurality of recesses (in the case of FIG. 1, thirteen recesses) spaced at predetermined intervals. Element chambers 91 in the form of a slit are formed between the members 87 and 90. Each element chamber 91 is provided so that the bottom surface thereof is located at the same height as the conveying surface. The hole of the inclined rotary cylinder 88 surrounds a discarding hole 92 for discarding the dry analysis elements 12 after measurement. The used dry analysis measurement 12 in the element chamber is moved as it is towards the center of the rotary member and dropped through the discarding hole 92 for disposal.

The upper member 90 comprises a heater (not shown) for incubating the dry analysis elements 12 within the element chamber 91 at a predetermined temperature by the temperature control by the heater. The upper member 90 further comprises a retaining member 93 which faces the element chamber 91 and retains the mount of the dry analysis element 12 to prevent evaporation of the sample. A heat insulating cover 94 is provided on the upper surface of the upper member 90, and the entire first incubator 4 is covered with a light shielding cover 95. Further, a photometric opening 91*a* is formed in the center of the bottom surface of each element chamber 91 of the rotary member 87. The reflection density of the dry analysis element 12 is measured through the photometric opening 91*a* by a photometer head 96 disposed at the position shown in FIG. 1. The first incubator 4 is rotated in both directions by a belt mechanism (not shown)

The element discarding mechanism 10 comprises a discarding bar 101 which can advance into or withdraw from the element chamber 91 in a radial direction. The discarding bar 101 is fastened at the rear end to a horizontally running belt 102, and pushes the measured dry analysis element 12 out of the element chamber 91 depending on the movement of the belt 102 driven by a driving motor 103. A collection box is provided under the discarding hole 92 for collecting the dry analysis elements 12 after being subjected to measurements.

In the second incubator 4 for measuring the ion activity, a single element chamber is defined between the recess formed at the bottom of the first element retainer 63 of the aforementioned sliding frame 62 and the upper surface of a measurement body 97. The second incubator 5 is provided with a heater (not shown) so that the portion of the dry analysis element 12 where the ionic activity is measured is incubated at a predetermined temperature by the temperature control of the heating means. Three potential measuring probe pairs 98 for measuring the ion activity are positioned in the side wall of the measurement body 97 so that they can be brought into contact with the ion selective electrodes of the electrolytic dry analysis element 12.

The blood filtering unit is inserted into the sample container (e.g., a blood-collecting tube) 11 held in the sample tray 2 and suctions plasma through a holder (not shown) with a glass fiber filter which is mounted on the upper end of the sample container, thereby separating plasma from the blood and holding the separated plasma in a cup formed on the top of the holder.

In the following, the first embodiment of the position restricting structure for the dry analysis element 12, when the element cartridge 13 is loaded in the sample tray 2 of the biochemical analysis apparatus 1 such as described hereinabove, will be explained with reference to FIGS. 4, 5, 6A and 6B.

As shown in FIG. 4, the penetration path 13*c*, which is a slit formed in the element cartridge, and the rotary disk 21 of the sample tray 2 are provided with a mechanism for pushing back a dry analysis element 12 into the element cartridge 13 so as to align the upper elements held therein if the element 12 projects outward from the element take-out port 13*a* when the element cartridge 13 holding therein the dry analysis elements 12 is mounted from above to the element mounting section 24 of the sample tray. This mechanism comprises a restricting projection 32 formed as a tapered rib that penetrates into the penetration path 13*c* when the cartridge is loaded, to contact and return the outwardly projecting dry analysis element 12.

The penetration path 13*c* of the element cartridge 13 is provided, as shown in FIG. 4, so as to extend vertically from the element take-out port 13*a* in the lower end part of (in the direction of loading the cartridge) the front wall of the cartridge while inwardly passing through the front wall. Here, two penetration paths are provided, one near each side. The bottom wall of the element cartridge 13, provided at the lower part of the element take-out port 13*a* so as to be positioned lower than the penetration path 13*c*, is cut-away to allow the aforementioned restricting projection 32 to penetrate into the penetration path 13*c* from the bottom end thereof. The opposites sides at the lower part of the penetration path 13*c* extending to the element take-out port 13*a* are inclined to diverge from one another towards their bottom so as to form inclined guide surfaces for guiding the restricting projection 32 to penetrate therein.

On the other hand, the restricting projection 32 of the sample tray 2 is disposed on a radially outside inner surface of each element mounting section 24 of the rotary disk 21, that is, the inner surface of the peripheral wall of the rotary disk 21, and vertically extends above the element outlet 21*a*. The restricting projection 32 is formed in a taper shape having a smaller projecting height at its upper part and a larger projecting height at its lower part. The thickness of the restricting projection 32 is smaller than the slit width of the penetration path 13c of the element cartridge 13 mentioned above. The projecting amount (projecting height) at the lower end of the restricting projection is formed such that the lower end substantially reaches the inner surface of the front wall of the element cartridge 13 when the cartridge is mounted as shown in FIG. 6B. With the difference in dimension between the element mounting section 24 and the element cartridge 13 taken into account and the like, the projecting height is basically formed to be slightly larger than the wall thickness of the element cartridge 13. This projecting height is designed depending on the allowable deviation amount from the proper position of the dry analysis element 12, i.e. the relationship with the readable range of an information readout apparatus and the like.

When the element cartridge 13 is loaded in place (see FIG. 6B), the upper end of the element outlet 21a in the peripheral wall of the sample tray 21 is located at the same or a higher level than that of the upper end of the element take-out port 13a, so that the lowermost dry analysis element 12 can pass through the outlet. Meanwhile, when the element cartridge 13 is loaded in place, the lower end of the restricting projection 32 is located at a higher level than that of the top surface of the lowermost dry analysis element 12, and does not interfere with the dry analysis element 12 such that the element can be removed therefrom.

In the following, the operations for loading the element cartridge 13 in the element mounting section 24 of the sample tray 2 will be described in connection with FIGS. 6A and 6B. As shown in FIG. 6A, the element cartridge 13 holding therein the dry analysis elements 12 is mounted to the element mounting section 24 from above. At this time, the lowermost dry analysis element 12 may slip and project outward from the element take-out port 13a. As the element cartridge 13 is mounted, the projecting edge portion of the dry analysis element 12 abuts the upper part of the taper constituting the restricting projection 32, and then as the dry analysis element 12 slides along the tapered surface by the further downward movement of the cartridge, the element is pushed into the cartridge by the tapered surface with the gradually increasing amount of protrusion. When the element cartridge 13 reaches the bottom of the element mounting section 24 (see FIG. 6B), the dry analysis element 12 is pushed back to its proper position similar to that of the upper dry analysis elements 12 and aligned to the upper elements. With this, reading the analysis information carried on the lower surface of the lowermost element become possible, contact with the restricting projection 32 is released, and the element can be removed out of the element take-out port. In addition, the position of the element cartridge 13 is also restricted.

On the other hand, as shown in FIGS. 4 and 5, when the element cartridge 13 can not be-mounted to the element mounting section 24 because the dry analysis element 12 considerably projects outward from the element take-out port 13a of the element cartridge and interferes with the peripheral wall-of the rotary disk 21, it is necessary to use a finger or the like to push back the projecting portion of the dry analysis element 12 to the extent that the edge of the element 12 becomes substantially flush with the outer surface of the cartridge before loading the element cartridge 13. When loading the cartridge, the dry analysis element 12 is pushed further inward and aligned with the same proper position with other upper dry analysis elements 12.

In the aforementioned embodiment, the element cartridge 13 has two penetration paths 13c positioned one near each side. However, the number of the penetration paths may be one or more than two. Besides the slit groove, the penetration path 13c may be of any shapes by which the restricting member 32 can penetrate the penetration path and contact the dry analysis elements 12. For the restricting member 32, the number thereof may be one or more than two. Additionally, the restricting member may be an arc-shaped projection, as long as the amount of protrusion thereof gradually increases along the loading direction of the element cartridge 13. Alternatively, the restricting member may be a projection in the form of a rotating or non-rotatable roller, besides the tapered rib projection.

Figure 7:
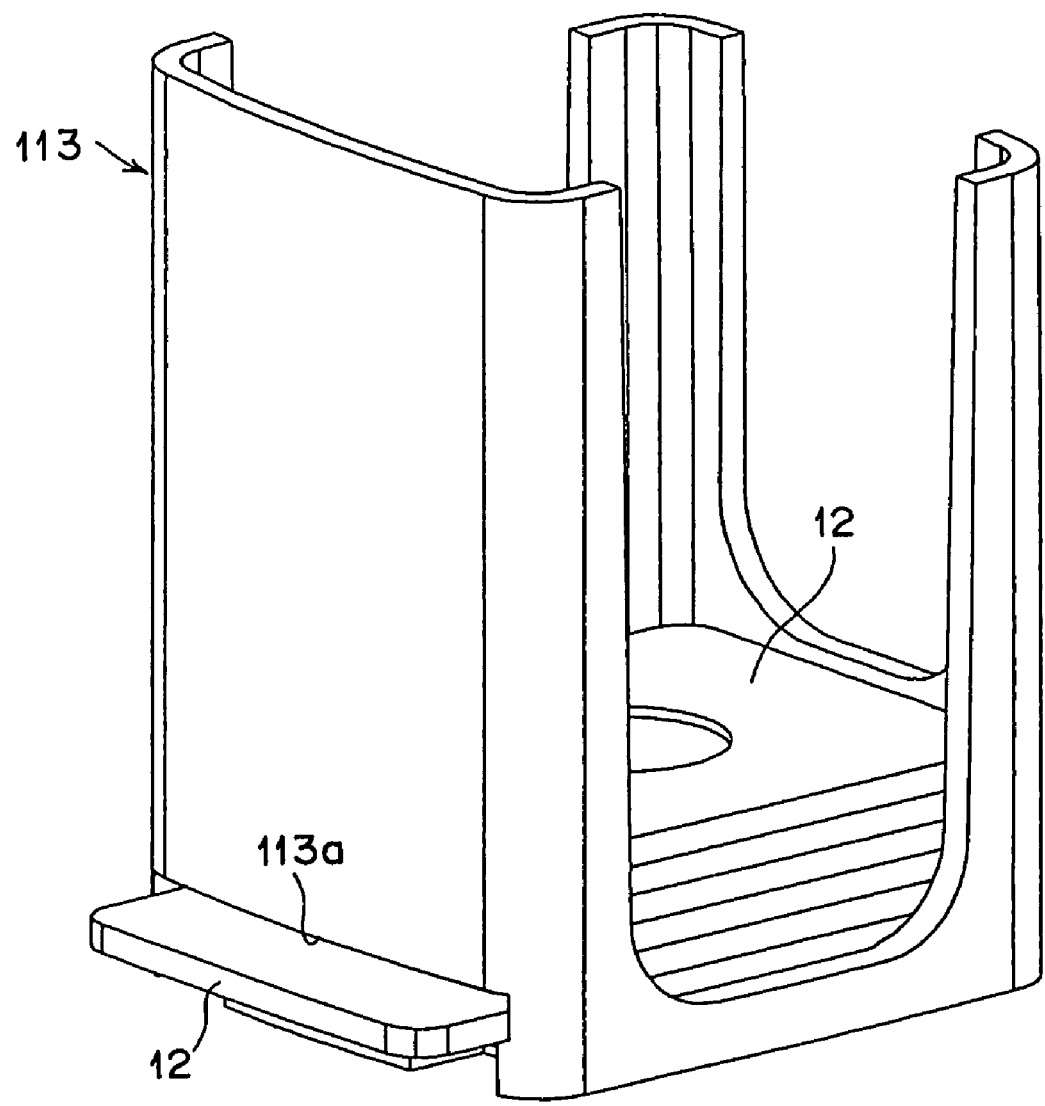
FIG. 7 is a perspective view showing an element cartridge according to a second embodiment of the present invention.
Figure 8A:
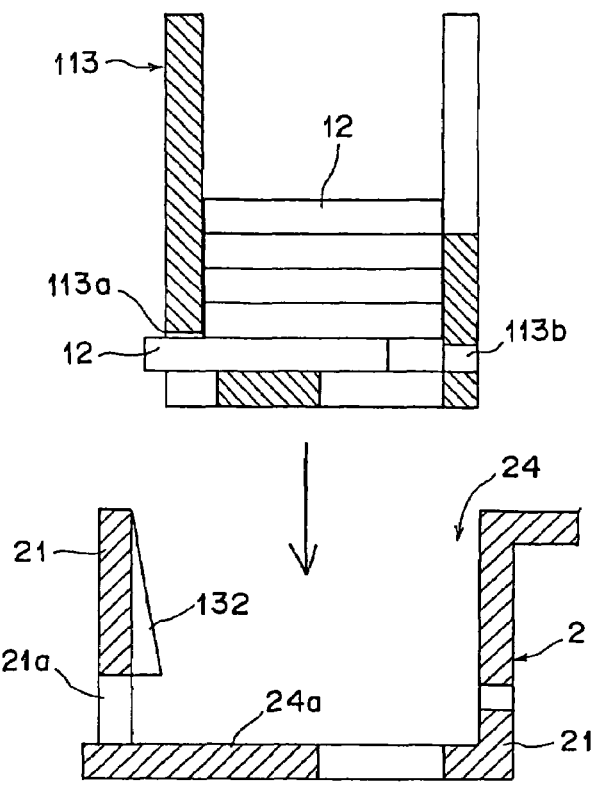
FIGS. 8A and 8B are schematic views showing the correcting operation with respect to the dry analysis element associated with the loading operation of the element cartridge according to the second embodiment.
Figure 8B:
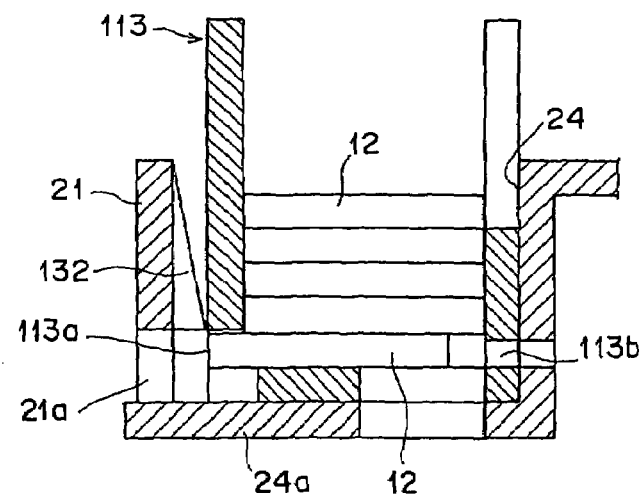

Next, the second embodiment of the position restricting structure for the dry analysis element 12 will be described with reference to FIGS. 7, 8A and 8B. FIG. 7 is a perspective view of the element cartridge 13 according to the second embodiment. FIGS. 8A and 8B are schematic views showing the correcting operation with respect to the dry analysis element associated with the loading operation of the element cartridge according to the second embodiment.

The element cartridge 113 of the second embodiment is the same as the element cartridge 13 of the first embodiment, without the penetrating path 13c. That is, the element cartridge 113 is only provided with an element take out port 113a at the lower end of its front surface, and an opening 113b (see FIGS. 8A and 8B) for the element transfer member 71 to penetrate through.

A restricting projection 132 in the form of a tapered rib is provided in the element mounting portion 24. The restricting projection 132 serves as a correcting means for pushing a projecting dry analysis element 12 back into a predetermined position within the element cartridge 113, during loading of the element cartridge 113 onto the sample tray 2.

The restricting projection 132 is of a lower height than the restricting projection 32 of the first embodiment. However, the position and the shape thereof are roughly the same. The restricting projection 132 extends in the vertical direction on the inner wall of the element mounting portion 24 above the element outlet 21a. The restricting projection 132 is tapered such that the amount of protrusion is low at the upper portion and high at the lower portion. The amount of protrusion (projection height) at the lower portion is set so that the restricting projection 132 reaches the surface of the front wall of the element cartridge 113 in the cartridge mounted state shown in FIG. 8B.

As shown in FIG. 8A, the element cartridge 113 holding therein the dry analysis elements 12 is mounted to the element mounting section 24 from above. At this time, the lowermost dry analysis element 12 may slip and project outward from the element take-out port 113a. As the element cartridge 113 is mounted, the projecting edge portion of the dry analysis element 12 abuts the upper part of the taper constituting the restricting projection 132. Then, as the dry analysis element 12 slides along the tapered surface by the further downward movement of the cartridge 113, the element is pushed into the cartridge 113 by the tapered surface with the gradually increasing amount of protrusion. When the element cartridge 113 reaches the bottom of the element mounting section 24 (see FIG. 8B), the dry analysis element 12 no longer projects from the element take out port 113a.

In the second embodiment, the distance that the dry analysis element 12 is pushed back is not as great as that in the first embodiment. However, regarding dry analysis elements 12 in this state, a readable range of the information readout apparatus is set, while the size and position of the bottom openings of the cartridge 113 and the element mounting portion 24 are also considered.

Figure 9A:
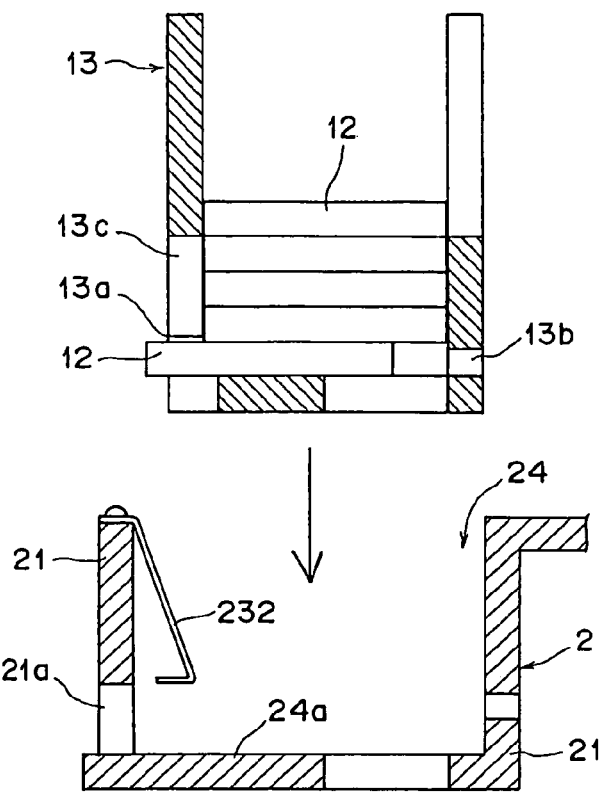
FIGS. 9A and 9B are schematic views showing the correcting operation with respect to the dry analysis element associated with the loading operation of the element cartridge according to a third embodiment of the present invention.
Figure 9B:
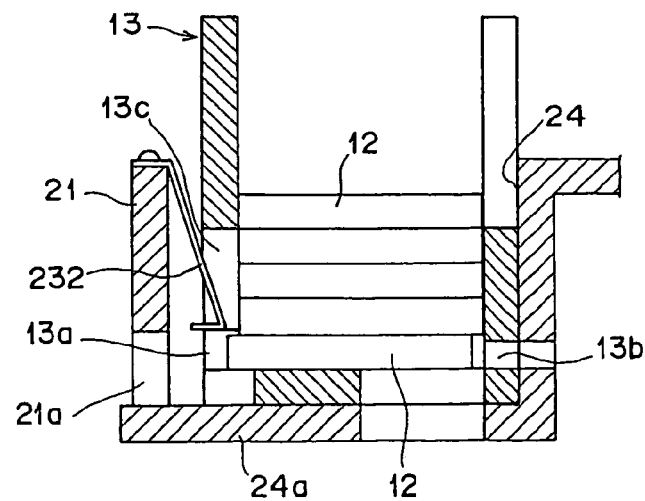

Next, the third embodiment of the position restricting structure for the dry analysis element 12 will be described with reference to FIGS. 9A and 9B. FIGS. 9A and 9B are schematic views showing the position correcting operation with respect to the dry analysis element associated with the loading operation of the element cartridge according to the third embodiment.

The element cartridge 13 of the third embodiment is the same as the element cartridge 13 of the first embodiment, and comprises the element take out port 13a and the penetrating path 13c in communication therewith at the front side thereof. In addition, the opening 13b, for the element transfer member 71 to penetrate through, is provided at the rear side thereof.

A restricting projection 232 in the form of a spring member is provided in the element mounting portion 24, as a correcting means of the present embodiment. The restricting projection 232 is provided so that the upper end of a spring plate is fixed above the element outlet 21a on the inner wall of the element mounting portion 24. The lower end of the plate spring protrudes into the interior of the element mounting portion 24, to form a taper. The protruding portion of the plate spring is capable of entering the penetration path 13c. The amount of protrusion (projection height) at the lower portion varies with elastic deformation of the spring when in contact with the dry analysis element 12. However, it is set so that the restricting projection 232 is positioned between the outer and inner surfaces of the front wall of the element cartridge 13 in the cartridge mounted state shown in FIG. 9B.

The operation of pushing and returning a projecting dry analysis element 12 associated with the loading operation of the element cartridge 13 into the element mounting portion 24 in the third embodiment is the same as that of the first embodiment illustrated in FIG. 6. In addition, the restricting projection 232 formed from the spring member is capable of elastically deforming when it contacts the projecting dry analysis element 12 or a portion of the element cartridge 13, during loading of the cartridge 13 into the element mounting portion 24. Therefore, this construction prevents excessive force from being exerted on the dry analysis element 12 and the element cartridge 13.

Note that in addition to the restricting projection 232 formed entirely from a spring member, correcting means may be constructed that incorporate spring members therein. For example, it is possible to provide swinging or retractable correcting members which are urged by spring members. Further, the restricting projection 232 is also applicable to the element cartridge 113, in which the penetration path 13c has not been formed, as shown in FIG. 7. In this case, the restricting projection 232 serves to eliminate projection of the dry analysis element 12 from the element take out port 113a.

Figure 10A:
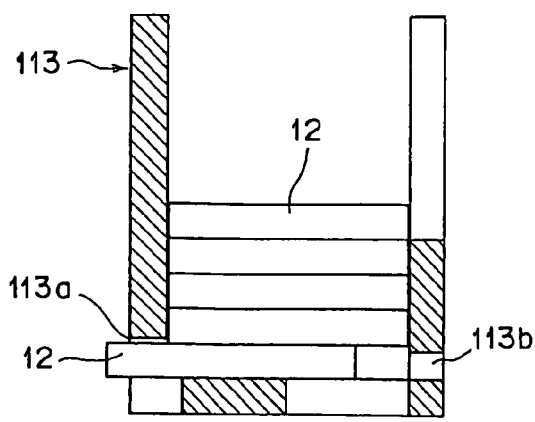
FIGS. 10A and 10B are schematic views showing the correcting operation with respect to the dry analysis element associated with the loading operation of the element cartridge according to a fourth embodiment of the present invention.

Next, the fourth embodiment of the position restricting structure for the dry analysis element 12 will be described with reference to FIGS. 10A and 10B. FIGS. 10A and 10B are schematic views showing the correcting operation with respect to the dry analysis element associated with the loading operation of the element cartridge according to the fourth embodiment.

In the fourth embodiment, a pusher 332 is provided as the correcting means. The pusher 332 is provided on the outer wall of the element mounting portion with respect to the rotary disc 21. The base of the pusher 332 is rotatably supported by a shaft 332a, to enable an arcuate extension (pushing portion) 332b to enter the element mounting portion 24 through the element outlet 21a. The pushing portion 332a can then push and return a dry analysis element 12 that projects from an element take out port 113a of a loaded element cartridge 113. The pusher 332 is driven by a motor or the like (not shown), which operates in association with the loading of the element cartridge 113 onto the element mounting portion 24.

A sensor 333 for detecting loading of an element cartridge 13 (an optical sensor, a proximity sensor, a contact switch or the like) may be provided at the bottom of the element mounting portion 24, to operate the pusher 332 based on a detection result, for example. Alternatively, a sensor member for mechanically detecting loading of the element cartridge 13 may be provided at the bottom or at a side of the element mounting portion 24. This sensor member may be caused to move when it abuts a portion of the element cartridge 13. The pusher 332 may be mechanically linked to the sensor member via a link or the like, to cause the pusher 332 to move in the pushing direction.

Figure 10A:
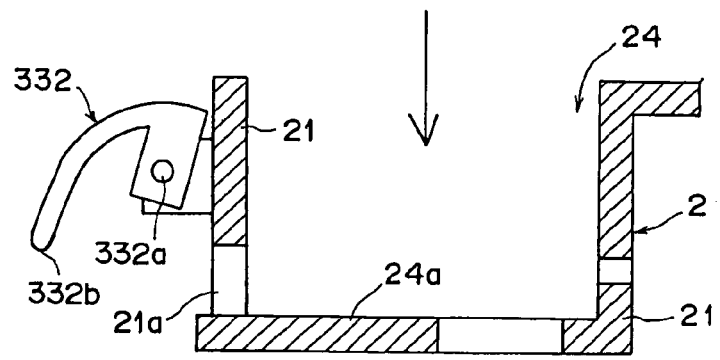
Figure 10B:
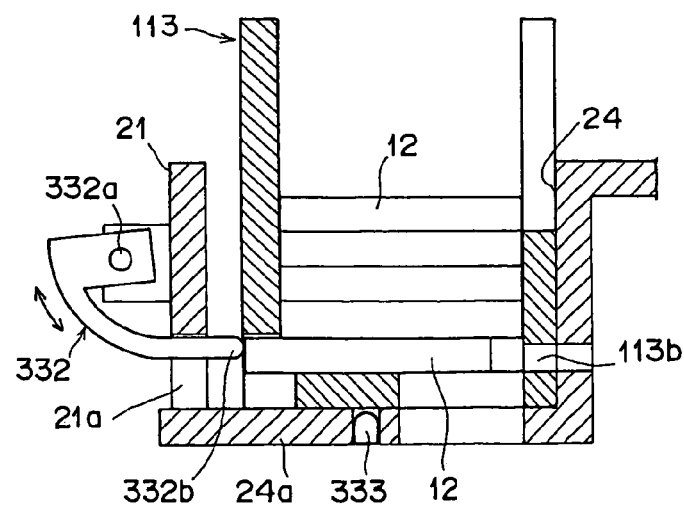

In the fourth embodiment illustrated in FIG. 10, the distance that the dry analysis element 12 is pushed back is just sufficient to return it so that it does not project from the element take out port 113a. However, a construction maybe adopted wherein the dry analysis element 12 is pushed back into the interior of the element cartridge 13. Note that it is necessary for the pusher 332 to be constructed such that it is capable of evacuating the element outlet 21a, so as to not interfere with removal of the dry analysis element.

What is claimed is:

1. An analysis apparatus for: mounting an element cartridge holding dry analysis elements required for measurement of a sample onto an element mounting portion, the element cartridge being equipped with an element take-out port which allows a single dry analysis element to pass through; removing one or more of the dry analysis elements from the element mounting portion; and conveying the one or more removed dry analysis elements to a following process; wherein
the element mounting portion has a correcting means for returning a protruding dry analysis element to a predetermined position within the element cartridge, in association with the loading operation of the element cartridge when the element cartridge is mounted on the element mounting portion.

2. An analysis apparatus as defined in claim 1, wherein:
the element cartridge is further equipped with a penetration path extending to the element take-out port in the cartridge loading direction; and
the element mounting portion is equipped with a correcting means for entering the penetration path, abutting a dry analysis element which protrudes into the element take out port, and pushing the dry analysis element to the predetermined position within the element cartridge, in association with the loading operation of the element cartridge when the element cartridge is mounted on the element mounting portion.

3. An analysis apparatus as defined in claim 1, wherein the correcting means comprises a restricting projection that tapers to protrude further outward as it extends.

4. An analysis apparatus as defined in claim 2, wherein the correcting means comprises a restricting projection that tapers to protrude further outward as it extends.

5. An analysis apparatus as defined in claim 1, wherein the correcting means comprises a spring member for pressing and urging an element cartridge.

6. An analysis apparatus as defined in claim 2, wherein the correcting means comprises a spring member for pressing and urging an element cartridge.

7. An analysis apparatus as defined in claim 2, wherein the penetration path for element cartridges comprises a slit groove.

8. An analysis apparatus as defined in claim 1, wherein:
the element mounting portion is equipped with an element outlet for a dry analysis element, which has been removed from an element cartridge mounted thereon, to pass through; and
the correcting means is provided above the element outlet of the element mounting portion so as to extend vertically.

9. An analysis apparatus as defined in claim 2, wherein:
the element mounting portion is equipped with an element outlet for a dry analysis element, which has been removed from an element cartridge mounted thereon, to pass through; and
the correcting means is provided above the element outlet of the element mounting portion so as to extend vertically.

10. An analysis apparatus as defined in claim 3, wherein:
the element mounting portion is equipped with an element outlet for a dry analysis element, which has been removed from an element cartridge mounted thereon, to pass through; and
the correcting means is provided above the element outlet of the element mounting portion so as to extend vertically.

11. An analysis apparatus as defined in claim 5, wherein:
the element mounting portion is equipped with an element outlet for a dry analysis element, which has been removed from an element cartridge mounted thereon, to pass through; and
the correcting means is provided above the element outlet of the element mounting portion so as to extend vertically.

12. An analysis apparatus as defined in claim 7, wherein:
the element mounting portion is equipped with an element outlet for a dry analysis element, which has been removed from an element cartridge mounted thereon, to pass through; and
the correcting means is provided above the element outlet of the element mounting portion so as to extend vertically.

13. An analysis apparatus as defined in claim 2, wherein the penetration path includes inclined guide surfaces at the lower part thereof which extend to the element take-out port so as to diverge from one another.

14. An analysis apparatus as defined in claim 7, wherein the penetration path includes inclined guide surfaces at the lower part thereof which extend to the element take-out port so as to diverge from one another.

15. An analysis apparatus as defined in claim 8, wherein:
when the element cartridge is loaded in place in the element mounting portion, the upper end of the element outlet of the element mounting portion is located at the same or higher level than that of the upper end of the element take-out port;
the lowermost dry analysis element passes through the outlet; and
the lower end of the restricting projection is located at a higher level than that of the top surface of the lowermost dry analysis element.

16. An analysis apparatus as defined in claim 9, wherein:
when the element cartridge is loaded in place in the element mounting portion, the upper end of the element outlet of the element mounting portion is located at the same or higher level than that of the upper end of the element take-out port;
the lowermost dry analysis element passes through the outlet; and
the lower end of the restricting projection is located at a higher level than that of the top surface of the lowermost dry analysis element.

17. An analysis apparatus for: mounting an element cartridge holding dry analysis elements required for measurement of a sample onto an element mounting portion; removing one or more of the dry analysis elements from the element mounting portion; and conveying the one or more removed dry analysis elements to a following process; wherein:
the element mounting portion is equipped with a pusher for pushing and returning a dry analysis element that protrudes from the element cartridge to a predetermined position within the element cartridge, in association with the loading operation of the element cartridge when the element cartridge is mounted on the element mounting portion.

18. An analysis apparatus as defined in claim 17, wherein:
the pusher operates after detecting mounting of the element cartridge on the element mounting portion.

* * * * *